United States Patent [19]

Gerhold

[11] Patent Number: 4,549,903
[45] Date of Patent: Oct. 29, 1985

[54] HERBICIDAL COMPOSITIONS OF ACIFLUORFEN OR SALTS THEREOF AND CITRATES

[75] Inventor: Norman R. Gerhold, Warrington, Pa.

[73] Assignee: Rohm and Haas Company, Philadelphia, Pa.

[21] Appl. No.: 538,312

[22] Filed: Oct. 3, 1983

[51] Int. Cl.$^4$ ............................................. A01N 37/38
[52] U.S. Cl. .......................................... 71/116; 71/91; 71/113; 71/DIG. 1
[58] Field of Search ..................... 71/DIG. 1, 116, 113

[56] References Cited

U.S. PATENT DOCUMENTS 3,585,022  6/1971  Gray ....................................... 71/65

FOREIGN PATENT DOCUMENTS 847370  9/1960  United Kingdom .

OTHER PUBLICATIONS

The Merck Index, 9th Edition, p. 2305, entry 2307.

*Primary Examiner*—Catherine L. Mills
*Attorney, Agent, or Firm*—Polly E. Ramstad

[57] ABSTRACT

Compositions comprising acifluorfen or one of its agronomically acceptable salts and a citrate salt, in a weight amount greater than the acifluorfen, exhibit enhanced herbicidal activity, particularly against velvetleaf.

18 Claims, No Drawings

HERBICIDAL COMPOSITIONS OF ACIFLUORFEN OR SALTS THEREOF AND CITRATES

TECHNICAL FIELD

This invention relates to methods for enhancing the herbicidal activity of acifluorfens and to herbicidal compositions having enhanced activity.

BACKGROUND OF THE INVENTION

Acifluorfen, 5-(2-chloro-4-trifluoromethyl-phenoxy)-2-nitrobenzoic acid, and its agronomically acceptable salts are selective diphenyl ether herbicides which have both pre- and post-emergence weed control. They are particularly useful in the post-emergence control of a wide variety of broadleaf weeds. However, there are some broadleaf weeds, for example, velvetleaf and common cocklebur, against which its herbicidal activity is considered inferior. Citrate salts per se have no significant herbicidal activity.

Copending U.S. patent application Ser. No. 99,769 filed Dec. 3, 1979, abandoned, by Gerald E. Kollman, discloses the use of an aqueous composition containing a water soluble salt of an inorganic or organic acid and acifluorfen, or an agronomically acceptable salt thereof, as a means for obtaining improved weed control including the control of velvetleaf. Additionally, sodium acifluorfen has been formulated with sodium citrate dihydrate to enhance the stability of the herbicide. However, the amount of citrate added has been generally less than about half the weight percent of the sodium acifluorfen present, which is insufficient to cause any beneficial effect on the activity of the herbicide.

The present invention recognizes that compositions of acifluorfen and its agronomically acceptable salts in combination with citrate salts have a particularly pronounced effect on enhancing the herbicidal activity of the acifluorfen and in broadening the spectrum of activity particularly against velvetleaf.

DESCRIPTION OF THE INVENTION

According to the invention, certain herbicidal compositions which comprise (a) acifluorfen or one of its agronomically acceptable salts and (b) a citrate in an amount equal to or greater than the weight amount of the acifluorfen, exhibit significantly greater herbicidal activity than would be expected from the herbicidal activity (or lack of activity) of the individual components of the composition. Herbicidal activity of acifluorfen or one of its salts against velvetleaf is particularly advantageously affected by this composition. Thus, the compositions of the invention permit a significantly greater degree of control of velvetleaf than what is obtained by using acifluorfen or one of its agronomically acceptable salts alone. The compositions are also beneficial to the activity of acifluorfens against other weeds, e.g., morningglory and cocklebur. In addition to the increased herbicidal activity, the compositions still retain selectivity.

The compositions of the invention can be applied in any amount which will provide the required control of weeds. The particular amount is dependent upon many factors including, for example, the crop, weeds sought to be controlled and environmental conditions. Once such factors are known, one in the art can readily determine the amount of the composition to be applied and the amount of the acifluorfen and citrate it should contain. The composition is generally applied in a manner so that from about 0.05 to about 13 kilograms (kg)/hectare (ha), preferable from about 0.1 to about 1.1 kg/ha and more preferably from 0.13 to about 0.55 kg/ha of acifluorfen or one of its agronomically acceptable salts is applied to the locus of the crop. The citrate is present in an amount which causes the herbicidal activity of the acifluorfen to be venefitted. Generally, the amount of citrate applied will be at least about 0.5 kg/ha and preferably will be at least 0.1 kg/ha and will not exceed about 13 kg/ha, preferably it will not exceed about 8 kg/ha and more preferably it will not exceed about 4.5 kg/ha. Most preferably, the amount of citrate applied will be between about 1 and about 2.2 kg/ha. The ratio of the acifluorfen to citrate in the composition is at least 1:1 and not greater than about 1:35 and preferably not greater than about 1:16.

It is preferred that an agronomically acceptable salt of acifluorfen be used. Such salts are disclosed in U.S. Pat. No. 4,063,929. Preferred salts of acifluorfen are the sodium, potassium and amine, including ammonium, salts. Amine salts include primary, secondary, tertiary and quaternary amine salts of acifluorfen. Preferred amine salts of acifluorfen include mono, di, tri or tetra substituted ($C_1$–$C_4$) alkylamines including dimethyl, diethyl and triethylamines; hydroxy ($C_2$–$C_4$) alkylamines including monoethanol and diethanolamines and, preferably, ammonium and ethylene oxide derivatives of fatty acids, fatty amides and fatty quaternaries including bis-polyoxyethylene(5) cocoamine and bis-polyoxyethylene(5) tallowamine salts. The more preferred salt is sodium acifluorfen. Citrate salts include alkali metal, alkaline earth metal and ammonium salts of citric acid. The preferred citrates are sodium citrates, potassium citrates and ammonium citrates. Ammonium citrate and diammonium citrate are more preferred.

The compositions of the invention are typically formulated as concentrated aqueous solutions, as soluble flowable powders containing both the herbicide and the citrate, or as separate concentrated solutions or soluble formulated powders, one containing the herbicide and the other the salt. The formulation can then be diluted to appropriate use concentrations with water. The concentrated solutions and the formulated powders are diluted with water to give a carrier volume of generally about 5 to about 50 gallons per acre at the desired rate of application of the herbicide.

The compositions of the invention are useful as pre-emergence and, more preferably, as postemergence herbicides. Among the crops on which the compositions of this invention can be advantageously employed are, for example, cotton, soybeans, peanuts, safflower, beans, rice, peas, carrots, corn, wheat, sunflowers and other cereal crops. Soybeans, peanuts, sunflowers and rice are preferred crops.

A composition of the invention can be applied to the growth medium or, preferably, to plants to be treated either by itself or, as is generally done, in a form which also comprises as agronomically-acceptable carrier. By agronomically acceptable carrier is meant any substance which can be used to dissolve, disperse or diffuse a herbicidal compound, e.g., acifluorfen and the citrate, without impairing the effectiveness of the herbicidal compound and which by itself has no deterimental effect on the soil, equipment, crops, or agronomic environment. Mixtures of the compositions of the invention may also be used in any of these herbicidal formulations.

Compositions of the invention can also be mixed with or used in conjugation with the herbicide bentazone, 3-isopropyl-(1H)-benzo-2,1,3-thiadiazin-4-one-2,2-dioxide.

When it is desirable, particularly in postemergence applications, adjuvants, such as dispersing agents, stickers, adhesives, and the like, may be included in accordance with agricultural practices. Examples of adjuvants which are commonly used in the art can be found in the John W. McCutcheon, Inc. publication "Detergents and Emulsifiers Annual". The addition of a wetting agent to the composition can result in increased phytotoxicity. Consequently, if it is necessary to add a wetting agent to the composition, it generally should not exceed about 0.05 (v/v)% and preferably should not exceed about 0.03 (v/v)%.

The compounds of the invention are generally applied to the area of treatment as herbicidal sprays by methods commonly employed, such as conventional high-gallonage hydraulic sprays, low gallonage sprays, airblast spray, aerial sprays and dusts. For low volume applications, a solution of the composition is usually used. The dilution and rate of application can be varied and will usually depend upon such factors as the type of equipment employed, the method of application, the area to be treated and the type and stage of development of the weeds.

EXAMPLE 1

This example shows the significantly greater enhancement in herbicidal activity of sodium acifluorfen obtained by combining it with various citrates.

Formulations of sodium acifluorfen were prepared by dissolving sodium acifluorfen in water in an amount to obtain about a 21 (w/v)% solution (Na acifluorfen-T) and by dissolving sodium acifluorfen and sodium citrate dihydrate in water to obtain concentrations of about 21 (w/v)% and 8.8 (w/v)%, respectively (Na acifluorfen-C). Additional aqueous formulations were prepared by adding different citrate salts to these aqueous solutions of sodium acifluorfen. The formulations were tested under greenhouse conditions using the following test. Seeds of soybeans (*Glycine max*) and velvetleaf (*Abutilon theophrasti*) were planted in soil in plots. The seeds were allowed to germinate and after about two weeks the plots were treated with the test formulations. The day of treatment could vary within a 14–24 day period following the planting of the seeds because plants of each crop and weed species were selected for uniformity, size and stage of development. The formulations were applied using a sprayer at a volume of 25 to 50 gallons per acre. About two weeks after the test formulations were applied, the state of the growth of the plants was observed and the phytotoxic effect of each formulation was evaluated on a scale of 0 to 100; 0 indicates no control and 100 indicates 100% control (complete control). The rates of application and typical results obtained are presented in Table 1. None of the citrates when applied alone cause any significant injury to either the soybeans or velvetleaf weeds.

TABLE 1

| | Composition | Rate lb/A (Herb. + Salt) | % Injury SOY | % Control VEL |
|---|---|---|---|---|
| Test 1 | Na Acifluorfen-C | .25 | 0 | 30 |
| | w/NH$_4$ Citrate | .25 + 1.0 | 4 | 68 |
| | w/(NH$_4$)$_2$ Citrate | .25 + 1.0 | 3 | 83 |
| | w/(NH$_4$)$_3$ Citrate | .25 + 1.0 | 3 | 85 |
| Test 2 | Na Acifluorfen-T | .5 | 5 | —* |

TABLE 1-continued

| Composition | Rate lb/A (Herb. + Salt) | % Injury SOY | % Control VEL |
|---|---|---|---|
| | .25 | — | 20 |
| | .125 | — | 5 |
| w/NH$_4$ Citrate | .5 + 1.0 | 18 | — |
| | .25 + 1.0 | — | 98 |
| | .125 + 1.0 | — | 63 |
| w/(NH$_4$)$_2$ Citrate | .5 + 1.0 | 18 | — |
| | .25 + 1.0 | — | 85 |
| | .125 + 1.0 | — | 60 |
| w/(NH$_4$)$_3$ Citrate | .5 + 1.0 | 15 | — |
| | .25 + 1.0 | — | 88 |
| | .125 + 1.0 | — | 63 |
| w/Na Citrate | .5 + 1.0 | 15 | — |
| | .25 + 1.0 | — | 85 |
| | .125 + 1.0 | — | 50 |
| w/Na$_2$ Citrate | .5 + 1.0 | 15 | — |
| | .25 + 1.0 | — | 65 |
| | .125 + 1.0 | — | 45 |
| w/Na$_3$ Citrate | .5 + 1.0 | 10 | — |
| | .25 + 1.0 | — | 65 |
| | .125 + 1.0 | — | 25 |

*effect was not determined.

EXAMPLE 2

Using the same procedure as described in Example 1, the activities of sodium acifluorfen-T, sodium acifluorfen-C and each of these herbicides in conjunction with ammonium citrate were determined. An average of the results, expressed as an increase in percentage control over each herbicide alone, of the tests are provided in Table 2.

TABLE 2

| Composition | Rate lb/A Herb. + Salt | % Control Increase Over the Acifluorfen Alone SOY | VEL | No. of Tests Averaged |
|---|---|---|---|---|
| Na Acifluorfen-T | .25 + 1.0 | 4 | 48 | 13 |
| w/(NH$_4$)$_2$ Citrate | .25 + 2.0 | 16 | 59 | 3 |
| Na Acifluorfen-C | .25 + 1.0 | 5 | 49 | 5 |
| w/(NH$_4$)$_2$ Citrate | .25 + 2.0 | 6 | 60 | 11 |

EXAMPLE 3

The activities of sodium acifluorfen-T and sodium acifluorfen-C were determined in field tests. The procedure entailed preparing ground, which had a natural infestation of velvetleaf seeds from prior years, for planting of soybeans according to agronomical practices. About three weeks after the planting of the soybeans, when the soybeans were at their first trifoliate stage and the velvetleaf was at its two leaf stage, the field was divided into plots and different plots sprayed with each of the acifluorfens. About fourteen days after the application, the plants were observed and the phytotoxic effect of each formulation was evaluated on a scale of 0 to 100; 0 indicates no control and 100 indicates 100% control (complete kill). Typical results are presented below in Table 3 and show that there is no significant difference in the activities of these acifluorfens.

TABLE 3

| Composition | Rate lb/A | % Injury SOY | % Control VEL |
|---|---|---|---|
| Na Acifluorfen-T | 0.25 | 0 | 30 |
| | 0.50 | 4 | 67 |
| Na Acifluorfen-C | 0.25 | 3 | 35 |

TABLE 3-continued

| Composition | Rate lb/A | % Injury SOY | % Control VEL |
|---|---|---|---|
| | 0.50 | 0 | 63 |

What is claimed is:

1. A herbicidal composition comprising (a) a herbicide selected from the group consisting of acifluorfen and an agronomically acceptable salt thereof and (b) a citrate selected from the group consisting of alkali metal, alkaline earth metal and ammonium citrates wherein the citrate is present in a greater weight amount than the herbicide.

2. The herbicidal composition of claim 1 wherein the herbicide is selected from the group consisting of sodium, potassium and amine acifluorfens.

3. The composition of claim 1 wherein the citrate is selected from the group consisting of ammonium citrates, sodium citrates and potassium citrates.

4. The composition of claim 3 wherein the citrate is an ammonium citrate.

5. The composition of claim 3 wherein the ratio of herbicide to citrate is from about 1:1 to about 1:35.

6. A herbicidal composition comprising (a) sodium acifluorfen and (b) a citrate selected from the group consisting of ammonium citrates, sodium citrates and potassium citrates wherein the citrate is present in a greater weight amount than the sodium acifluorfen.

7. The composition of claim 6 wherein component (b) is an ammonium citrate and the ratio of sodium acifluorfen to the citrate is from about 1:1 to about 1:35.

8. The composition of claim 6 wherein the ratio of sodium acifluorfen to the citrate is from about 1:1 to about 1:16.

9. A method for enhancing the herbicidal activity of acifluorfen or one of its agronomically acceptable salts in a crop locus comprising applying to the crop locus a composition comprising (a) acifluorfen or one of its agronomically acceptable salts and (b) a water soluble citrate selected from the group consisting of alkali metal, alkaline earth metal and ammonium citrates wherein the citrate is present in a greater weight amount than the acifluorfen.

10. The method of claim 9 wherein the ratio of acifluorfen or one of its agronomically acceptable salts to component (b) is from about 1:1 to about 1:35.

11. The method of claim 10 wherein the acifluorfen is sodium acifluorfen.

12. The method of claim 10 wherein the acifluorfen is applied in an amount of from about 0.1 to about 1.1 kilograms per hectare and the citrate is applied in an amount of from about 1.0 to about 4.5 kilograms per hectare.

13. The method of claim 11 wherein the citrate is selected from the group consisting of ammonium citrates, sodium citrates and potassium citrates.

14. The method of claim 13 wherein the citrate is an ammonium citrate.

15. The method of claim 14 wherein the citrate is diammonium citrate.

16. A method for combating weeds in an agronomic crop comprising the improvement of postemergence application to the crop locus of a liquid form of a composition comprising (a) acifluorfen or an agronomically acceptable salt thereof and (b) a citrate selected from the group consisting of ammonium citrates, sodium citrates and potassium citrates wherein component (b) is present in a greater weight amount than component (a) and wherein the application of the composition results in an enhancement in the herbicidal activity of the acifluorfen.

17. The method of claim 16 wherein the acifluorfen is applied in an amount of from about 0.1 to about 1.1 kilograms per hectare and the citrate is applied in an amount of from about 1.0 to about 4.5 kilograms per hectare.

18. The method of claim 16 wherein the acifluorfen is applied in an amount of from about 0.13 to about 0.55 kilograms per hectare and the citrate is applied in an amount of from about 1.0 to about 2.2 kilograms per hectare.

* * * * *